US 8,129,692 B2

(12) United States Patent
Winfield et al.

(10) Patent No.: US 8,129,692 B2
(45) Date of Patent: Mar. 6, 2012

(54) METHOD FOR MONITORING FOULING IN A COOLING TOWER

(75) Inventors: Charles B. Winfield, Pasadena, TX (US); Lance Freeman, League City, TX (US); Stephen N. Harris, Houston, TX (US)

(73) Assignee: Quantum Technical Services, LLC, Sugar Land, TX (US)

( * ) Notice: Subject to any disclaimer, the term of this patent is extended or adjusted under 35 U.S.C. 154(b) by 627 days.

(21) Appl. No.: 12/248,315

(22) Filed: Oct. 9, 2008

(65) Prior Publication Data
US 2009/0099808 A1    Apr. 16, 2009

Related U.S. Application Data

(60) Provisional application No. 60/979,081, filed on Oct. 11, 2007.

(51) Int. Cl.
*G01T 1/00*    (2006.01)
(52) U.S. Cl. .................. 250/395; 250/356.1; 250/357.1; 250/358.1
(58) Field of Classification Search .................. 250/395, 250/356.1, 357.1, 358.1
See application file for complete search history.

(56) References Cited

U.S. PATENT DOCUMENTS

| | | | |
|---|---|---|---|
| 2,323,128 A | | 9/1941 | Hare |
| 3,136,892 A | | 6/1964 | Willett |
| 4,228,351 A | | 10/1980 | Snow |
| 4,283,629 A | | 8/1981 | Habermehl |
| 4,979,197 A | | 12/1990 | Troxler |
| 5,065,417 A | * | 11/1991 | Behringer et al. .............. 378/54 |
| 5,105,453 A | | 4/1992 | Hanrahan |
| 6,151,379 A | | 11/2000 | Kullenberg |
| 6,492,641 B1 | | 12/2002 | Dep |
| 6,507,025 B1 | | 1/2003 | Verbinski |
| 6,548,814 B1 | | 4/2003 | Gronli |
| 6,633,625 B2 | | 10/2003 | Jackson |
| 7,010,087 B2 | | 3/2006 | Robins |

FOREIGN PATENT DOCUMENTS
WO    WO 2007/060481    *  5/2007
* cited by examiner

*Primary Examiner* — David Porta
*Assistant Examiner* — Christine Sung
(74) *Attorney, Agent, or Firm* — John M. Lenczyk

(57) ABSTRACT

Fouling in the fill portion of a cooling tower is monitored by transmitting radiation through a cooling tower, detecting the amount of radiation that has penetrated the cooling tower, and calculating the density of the fill portion of the cooling tower based on the detected radiation. A higher than expected density indicates the presence of fouling on the fill portion of the cooling tower. A rate of fouling may be established by monitoring the density of the fill portion of the cooling tower over time.

3 Claims, 2 Drawing Sheets

METHOD FOR MONITORING FOULING IN A COOLING TOWER

This application claims priority from U.S. Provisional Application Ser. No. 60/979,081, filed on Oct. 11, 2007, which is hereby incorporated. herein by reference.

BACKGROUND

The present invention relates to cooling towers. More particularly, the present invention relates to direct or open-type cooling towers. Cooling towers rely on evaporation to remove heat from a stream of water (or other medium). In open cooling towers, the water to be cooled is exposed directly to the atmosphere. Typically, the warm water is sprayed over the top of a "fill" portion in the cooling tower while ambient air is blown through the fill. The fill is used to increase the contact area between the warm water and the (cooling) air, thereby providing greater heat transfer.

One problem associated with cooling towers is the build up of scale deposits on the fill (i.e. fouling). Minerals dissolved in the cooling water accumulate on the fill as the water evaporates. Buildup or fouling can significantly reduce the heat transfer and, therefore, reduce the efficiency of the cooling tower. Further, excessive fouling can even cause the fill portion to collapse due to the additional weight of the fouling material. It is therefore desirable to monitor the amount of fouling or buildup that occurs on the fill.

SUMMARY

In one embodiment of the present invention, a radioactive source-and a detector are placed on opposite sides of a cooling tower. The detector measures the amount of radiation transmitted through the fill in the cooling tower. The transmitted radiation is then converted to a density value. The measured density is then compared to a baseline density of (just) the fill in order to determine if fouling is present (i.e. a density that is higher than expected would indicate the presence of build-up or scaling). Further, the density may be measured at periodic intervals to determine a rate of fouling.

The technique is extremely non-intrusive because the measurements are typically taken along the external surfaces of the cooling tower while the cooling tower is in operation. Thus, in-situ density values may be obtained. Further, internal access to the cooling tower is not necessary, so there is minimal disruption to the process system. Also, the measurements may be taken at many different points through the fill material, yielding an overall "profile" of the cooling tower. As such, the technique does not rely on one measurement or sample point being representative of the entire fill, and asymmetrical or non-uniform scaling patterns can be readily detected.

DETAILED DESCRIPTION

Figure 1:
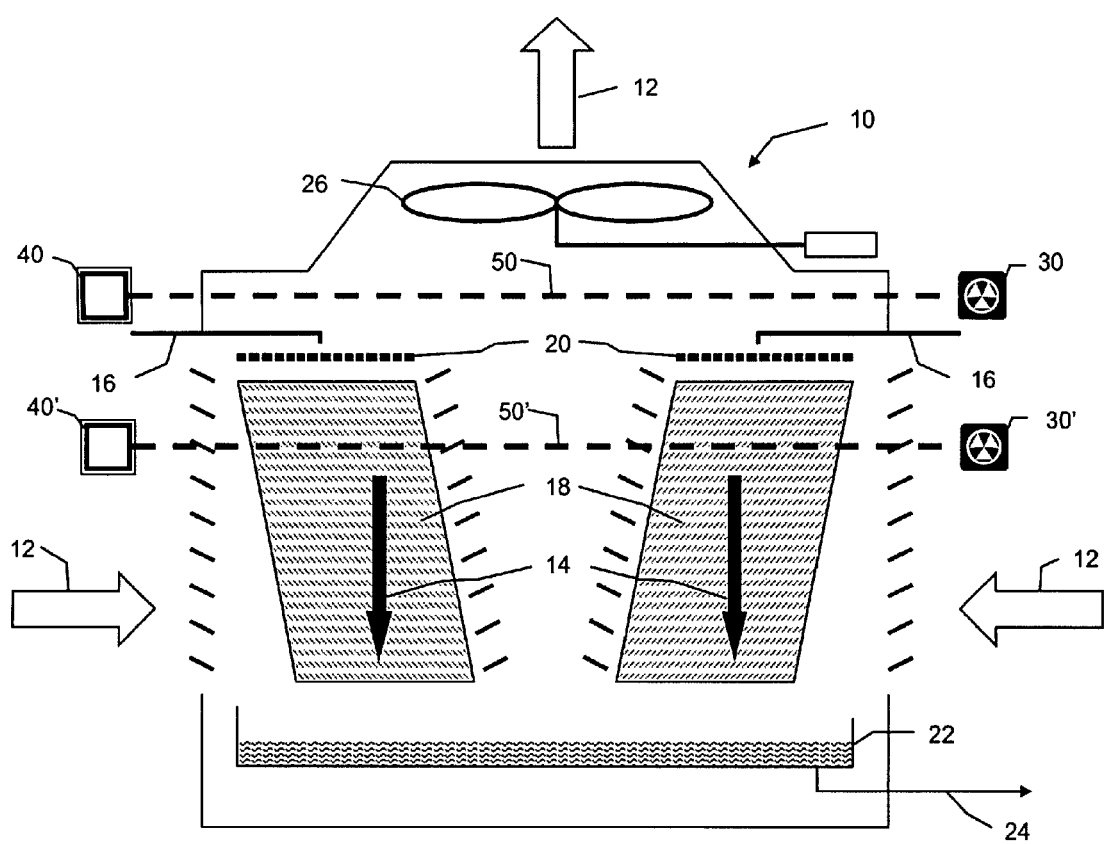
FIG. 1 is a side schematic view of a cooling tower showing the equipment used to perform the method of the present invention.

In one embodiment of the present invention, a method of monitoring fouling in a cooling tower is described. FIG. 1 shows a typical cooling tower 10. In this case, the cooling tower 10 is a cross-flow design with the flow of ambient air represented by the wide arrows 12 and the flow of water represented by the narrow arrows 14. Of course, the method also may be used with other cooling tower designs, such as counter-current flow types.

With reference to FIG. 1, a supply of hot water enters the cooling tower 10 through water inlets 16. The water is distributed over the fill 18 by distribution plates 20. Other means for distributing the water, such as a spray header, are also common. The water falls down through the fill 18, where it is cooled through the flow of air. The cooled water collects in a basin 22 below the fill 18 and exits the cooling tower 10 through a water outlet 24. A fan 26 helps drive the flow of air through the fill 18.

To monitor the fouling that occurs in the fill 18, a radioactive source 30 and a radiation detector 40 are positioned on opposite sides of the cooling tower 10. Preferably, the source 30 is a gamma-ray emitting source, such as Cesium-137, Cobalt-60 or Sodium-24. The activity of the source 30 is chosen based on the dimensions of the particular cooling tower 10. That is, the source 30 needs to be strong enough to be able to penetrate though the cooling tower 10 (and the fill 18) to the opposite side (where the detector 40 is positioned). Typically, the activity of the source 30 is between 50 millicuries (mCi) and 500 millicuries (mCi).

The detector 40 detects the gamma rays transmitted through the cooling tower 10 from the gamma source 30. Of course, if another type of radioactive source (i.e. x-ray emitting) is used, a suitable detector is used. A typical gamma ray detector is a 2-inch sodium iodide scintillation detector, such as the ones manufactured by Ludlum.

Although not shown in FIG. 1, a radiation counting device receives the signal from the detector 40. A Model 2200 Scalar Ratemeter by Ludlum is a typical type of counting device. The detector 40 and counting device measure the intensity of the gamma radiation transmitted through the cooling tower 10. For example, a typical counting device may display the measurement of the radiation intensity as counts of radiation per specified time period (e.g. 5,000 counts/6 seconds). A dashed line 50 is representative of the path of the radiation along which the intensity is measured.

According to the basic principles of radiation, the intensity of the radiation decreases as it passes through an absorbing material (e.g. the fill in the cooling tower). The decrease is dependent on the density and thickness of the absorbing material according to the following formula:

$$I = I_o e^{-\rho \mu x}$$

where $I_o$ is intensity of the initial radiation
  I is the intensity after passing through the absorbing material
  $\rho$ is the density of the absorbing material
  x is the thickness of the absorbing material and
  $\mu$ is an absorption coefficient Thus, the measured radiation can be converted into density, and the results may be reported as such. Abnormally high density measurements indicate the presence of additional material (e.g. fouling). The density readings can also indicate the severity of fouling.

Figure 2:
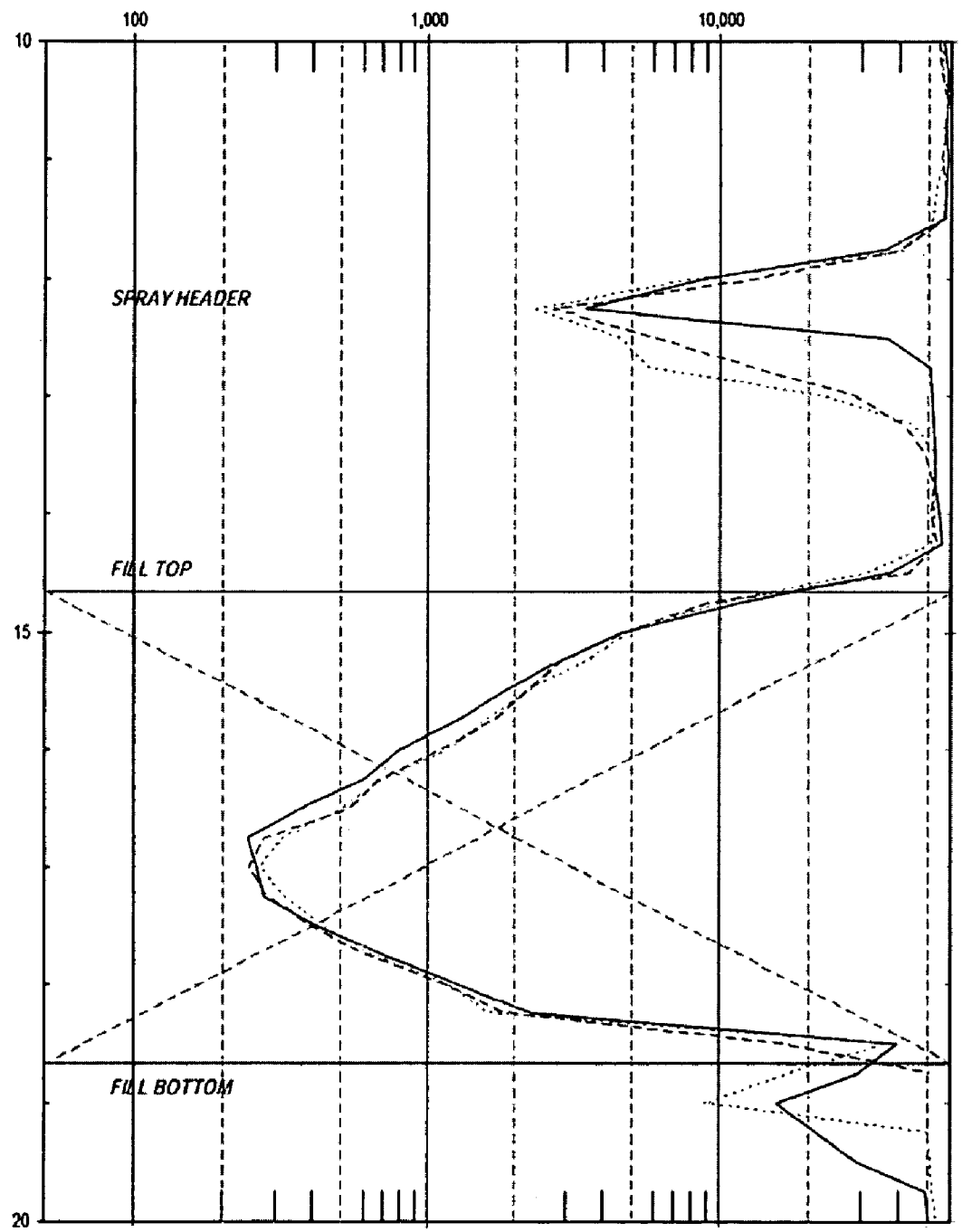
FIG. 2 is a plot of radiation intensities detected for a typical cooling tower

In a typical method for measuring the amount of fouling, the source 30 and detector 40 are positioned near the top of the cooling tower 10. The source 30 and detector 40 are each suspended from cables, wires or the like that are routed through a pulley system, which, in turn, allows the source and detector to be simultaneously raised or lowered along the sides of the cooling tower. Of course, other means for simultaneously raising or lowering the source and detector could alternatively be used. The source 30 and detector 40 are aligned with each other, such that the path of radiation (e.g. dashed line 50 in FIG. 1) is substantially horizontal. Beginning at the top of the cooling tower 10, the source 30 and detector 40 are simultaneously lowered past the fill 18 in successive increments. As the source 30 and detector 40 are lowered, the intensity of the radiation is noted or recorded. For instance, the radiation readings may be recorded by a computer. Generally, the source and detector are lowered in 3 inch increments. In other words, measurements are taken every 3 inches from top to bottom. Further, each individual reading is taken for a designated time interval. In most cases, the time interval for the readings is between 3 seconds and 6 seconds. FIG. 2 shows a typical representation of the radiation intensities measured through the cooling tower. The x-axis is the radiation intensity (e.g. counts of radiation per 6 seconds) and the y-axis is the elevation (e.g. feet). From the information displayed on the density profile of FIG. 2, the density value of the fill portion of the cooling tower can be calculated.

FIG. 1 shows the source 30 and detector 40 (with a dashed line 50 representing the path of the radiation) at a first position above the fill portion 18 of the cooling tower 10. In a second position, a dashed line 50' represents the path of radiation between the source 30' and detector 40' through the fill portion 18 of the cooling tower 10.

The first and second positions shown are indicative of the relative locations at which the radiation intensity may be measured in order to calculate an in-situ density value for the fill 18. The in-situ density refers to the density of the fill under current conditions (i.e. the density of the fill currently inside the cooling tower at the time the measurements are made). The first position is representative of a measurement of the amount of radiation detected through a portion of the cooling tower that does not contain fill, and the second position is representative of a measurement of the amount of radiation detected through the fill portion of the cooling tower. An in-situ density of the fill may be calculated from these measurements and the equation provided earlier. That is, a measurement of the radiation intensity through the fill portion would be I (e.g. 200-500 counts/6 seconds) and the measurement of the radiation intensity through the non-fill portion would be $I_o$ (e.g. 40,000 counts/6 seconds). The equation may be rearranged to solve for the density of the fill portion, as shown below, where x is the thickness of the fill between the source and detector, and $\mu$ is an absorption coefficient $$\rho = \frac{-\ln\frac{I}{I_o}}{\mu x}$$

Other than the presence of the fill, there are not many variables affecting the measurement taken at the first position compared to the measurement taken at the second position. For instance, the distance between the source and detector is unchanged, and the external structure of the cooling tower is unchanged. As such, it improves the accuracy of the density determination. That is, the accuracy is improved over a situation where there is not a non-fill portion of the cooling tower or it is not feasible to measure a non-fill portion of the cooling tower.

Once an in-situ density value of the fill portion of the cooling tower is calculated, it is compared to an established baseline density value for the fill portion in order to determine if fouling is present. If the in-situ density is greater than the baseline density, then it tends to indicate that fouling is present. Through repeated density measurements, the degree of fouling may also be established. For instance, over time, it is anticipated that periodic in-situ density measurements can establish a range of fouling, such as slight, moderate, severe or critical. For example, an in-situ density value that is 2 lbs/ft$^3$ higher than the baseline density value may be classified as slight fouling, 4 lbs/ft$^3$ may be classified as moderate fouling, and so on.

The baseline density value may be established in a variety of ways. For instance, the baseline density value may be established through appropriate specifications for the fill, in light of the operating conditions. That is, one may look up the density of the fill from specifications provided by the manufacturer of the fill, while adjusting the density to account for the rate at which water is circulating through the cooling tower. In other instances, the baseline density value may be established by measuring a sample of the fill. For example, a sample of a known volume of the fill may be weighed.

However, it is preferred that the baseline density value be established by transmitting and detecting radiation through the cooling tower when it is expected to be free of fouling. For example, a cooling tower that has just been thoroughly cleaned or a brand new cooling tower may be assumed to be free of fouling. Baseline density readings may be established by transmitting and detecting radiation through the new or recently cleaned cooling tower (preferably, through the fill portion and through a non-fill portion) and calculating the density of clean fill using the previously mentioned formula. A later in-situ density value can be measured and calculated in the same manner as the baseline density value to provide an accurate representation of the change in density (if any).

Over time, a number of in-situ density values may be established for the fill portion of a particular cooling tower by periodically transmitting and detecting radiation through the cooling tower. Further, the density values may be tracked over time to yield a rate of fouling in the fill portion. This information can be extremely useful in scheduling and planning maintenance shut-downs.

In one method of the present invention, the effectiveness of anti-fouling agents may be studied. It is known in the art that adding an anti-fouling agent to the water supply of a cooling tower can help remove and/or control fouling that occurs through the fill portion. However, there is a wide array of anti-fouling agents available, and it is difficult to verify the effectiveness of a particular anti-fouling agent. In one method, the effectiveness can be established by measuring a first density value of the fill portion by transmitting and detecting radiation through the cooling tower, then adding a quantity of an anti-fouling agent to the water supply, then measuring a second density value of the fill portion by transmitting and detecting radiation through the cooling tower after the anti-fouling agent has been added; and then comparing the second density value to the first density value. A decrease in density indicates that the anti-fouling agent is effective (because the fouling is reduced). A larger decrease in density would indicate a larger reduction of fouling.

The effective quantity of anti-fouling agent to be added can be optimized. For instance, after a second density value is measured and compared to the first density value, an additional quantity of anti-fouling agent is added. Then a third density value is measured and compared to the first and second density values. If, for instance, there is no decrease in density between the second and third density values, then it may be concluded that the additional quantity of fouling agent was unnecessary and wasteful. After repeating the steps of adding anti-fouling agent and then measuring a density value of the fill portion (by transmitting and detecting radiation through the cooling tower), a correlation between the quantity of anti-fouling agent and the resulting change in the density value of the fill portion may be established. With this correlation, the optimal amount of anti-fouling agent that should be added to the cooling tower water supply can be predicted from a measured density value. As such, the anti-fouling agent may be conserved.

Another benefit of the method of the present invention is that readings may be taken at several locations. For instance, once a first density profile from top to bottom is recorded, the source, detector, and accompanying equipment may be moved to a new position and again lowered in successive increments to obtain a second scan profile. This technique may be repeated, as desired. As such, the technique does not rely on one measurement or sample point being representative of the entire fill, and asymmetrical or non-uniform fouling can be readily detected. For instance, FIG. 2 shows a profile of radiation intensities for a typical cooling tower. The profile reveals that the intensity of radiation (i.e. the "counts") through the fill portion is inconsistent from top to bottom. There is a noticeable gradient of increasing intensities (decreasing density values) from the top of the fill downward, with the lowest intensities (and highest density values) situated just below the middle of the fill. By transmitting and detecting radiation at a number of points, it is less likely that a problem area will be missed.

It will be obvious to those skilled in the art that modifications may be made to the embodiments described above without departing from the scope of the invention as claimed.

What is claimed is:

1. A method for monitoring fouling in the fill portion of a cooling tower, comprising the steps of:

providing a cooling tower, said cooling-tower including a fill portion and a supply of water contacting said fill portion;

measuring a first density value of the fill portion by transmitting and detecting radiation through the cooling tower;

adding a quantity of anti-fouling agent to the water supply;

measuring a second density value of the fill portion by transmitting and detecting radiation through the cooling tower after said anti-fouling agent has been added; and comparing the second density value to the first density value in order to determine the effectiveness of the anti-fouling agent.

2. A method for monitoring fouling in the fill portion of a cooling tower as recited in claim 1, and further comprising the steps of:

adding an additional quantity of anti-fouling agent to the water supply; establishing a third density value of the fill portion by transmitting and detecting radiation through the cooling tower after said additional quantity of anti-fouling agent has been added; and comparing the third density value to the first and second density values in order to determine the effectiveness of the additional quantity of the anti-fouling agent.

3. A method for monitoring fouling in the fill portion of a cooling tower as recited in claim 2, and further comprising the steps of:

repeating the steps of adding a quantity of anti-fouling agent and then establishing a density value of the fill portion by transmitting and detecting radiation through the cooling tower; and establishing a correlation between the quantity of anti-fouling agent added to the water supply and the resulting change in the density value of the fill portion.

* * * * *